United States Patent
Grimard et al.

(10) Patent No.: US 6,585,741 B2
(45) Date of Patent: Jul. 1, 2003

(54) DEVICE FOR RASPING THE INTRAMEDULLARY CANAL OF A BONE AND METHOD FOR MANUFACTURING THE DEVICE

(75) Inventors: Jean-Christophe Grimard, Celletes (FR); Thierry Cousin, Menars (FR)

(73) Assignee: Sferic Sarl, Menars (FR)

( * ) Notice: Subject to any disclaimer, the term of this patent is extended or adjusted under 35 U.S.C. 154(b) by 0 days.

(21) Appl. No.: 09/908,738

(22) Filed: Jul. 20, 2001

(65) Prior Publication Data

US 2002/0019638 A1 Feb. 14, 2002

(30) Foreign Application Priority Data

Jul. 20, 2000 (FR) ............................................. 00 09527

(51) Int. Cl.$^7$ ............................................... A61B 17/00
(52) U.S. Cl. .......................................... 606/85; 606/79
(58) Field of Search ........................... 606/79; 144/168; 76/19, 13, 38, 115, 116, 81.2, 817; 407/6, 29.1, 62, 63, 64, 57

(56) References Cited

U.S. PATENT DOCUMENTS

| | | | | |
|---|---|---|---|---|
| 499,619 A | * | 6/1893 | Weed | 407/29.1 |
| 1,154,578 A | * | 9/1915 | Denly | 407/29.1 |
| 2,089,619 A | * | 8/1937 | Ripley | 407/29.1 |
| 2,214,954 A | * | 9/1940 | Crater | 407/29.1 |
| 2,455,064 A | * | 11/1948 | Johnson | 407/29.1 |
| 2,460,513 A | * | 2/1949 | Ferve | 407/29.1 |
| 3,005,478 A | * | 10/1961 | Laviano | 30/123 |
| 3,016,771 A | * | 1/1962 | Meissler et al. | 76/13 |
| 3,951,012 A | * | 4/1976 | Staley, Jr. | 407/29.1 |
| 4,427,872 A | | 1/1984 | Saunders | |
| 4,552,136 A | * | 11/1985 | Kenna | 606/80 |
| 4,601,289 A | * | 7/1986 | Chiarizzio et al. | 606/85 |
| 4,671,275 A | * | 6/1987 | Deyerle | 606/85 |
| 4,777,942 A | * | 10/1988 | Frey et al. | 409/178 |
| 5,006,121 A | * | 4/1991 | Hafeli | 606/79 |
| 5,047,033 A | * | 9/1991 | Fallin | 606/87 |
| 5,454,815 A | * | 10/1995 | Geisser et al. | 606/79 |
| 5,665,091 A | | 9/1997 | Noble et al. | |
| 5,919,007 A | * | 7/1999 | Brown | 29/76.1 |
| 5,993,455 A | * | 11/1999 | Noble | 606/79 |
| 6,120,508 A | * | 9/2000 | Grunig et al. | 606/79 |
| 6,319,256 B1 | * | 11/2001 | Spotorno et al. | 606/79 |

FOREIGN PATENT DOCUMENTS

| | | | |
|---|---|---|---|
| DE | 198 49 872 A1 | 5/2000 | |
| EP | 1 034 865 A1 | 9/2000 | |
| GB | 1383711 | * 2/1975 | B23D/43/00 |

* cited by examiner

Primary Examiner—Michael J. Milano
Assistant Examiner—P Roberts
(74) Attorney, Agent, or Firm—Nixon & Vanderhye

(57) ABSTRACT

The present invention relates to a machining method for obtaining a teeth following a helical curve on the surface of any shape whatsoever, this method being able to be applied to the manufacture of a broach, intended to prepare the intramedullary canal of a bone. The machining method on the surface of any shape whatsoever by a tool provided with a head, following at least one geometrical curve with the shape of a helix is characterised in that it comprises the following stages:

tracing the surface normal at a plurality of points taken along the helix, making the helix follow the head of the tool, by orienting the head in such a way that it follows the orientation of the defined normals.

14 Claims, 7 Drawing Sheets

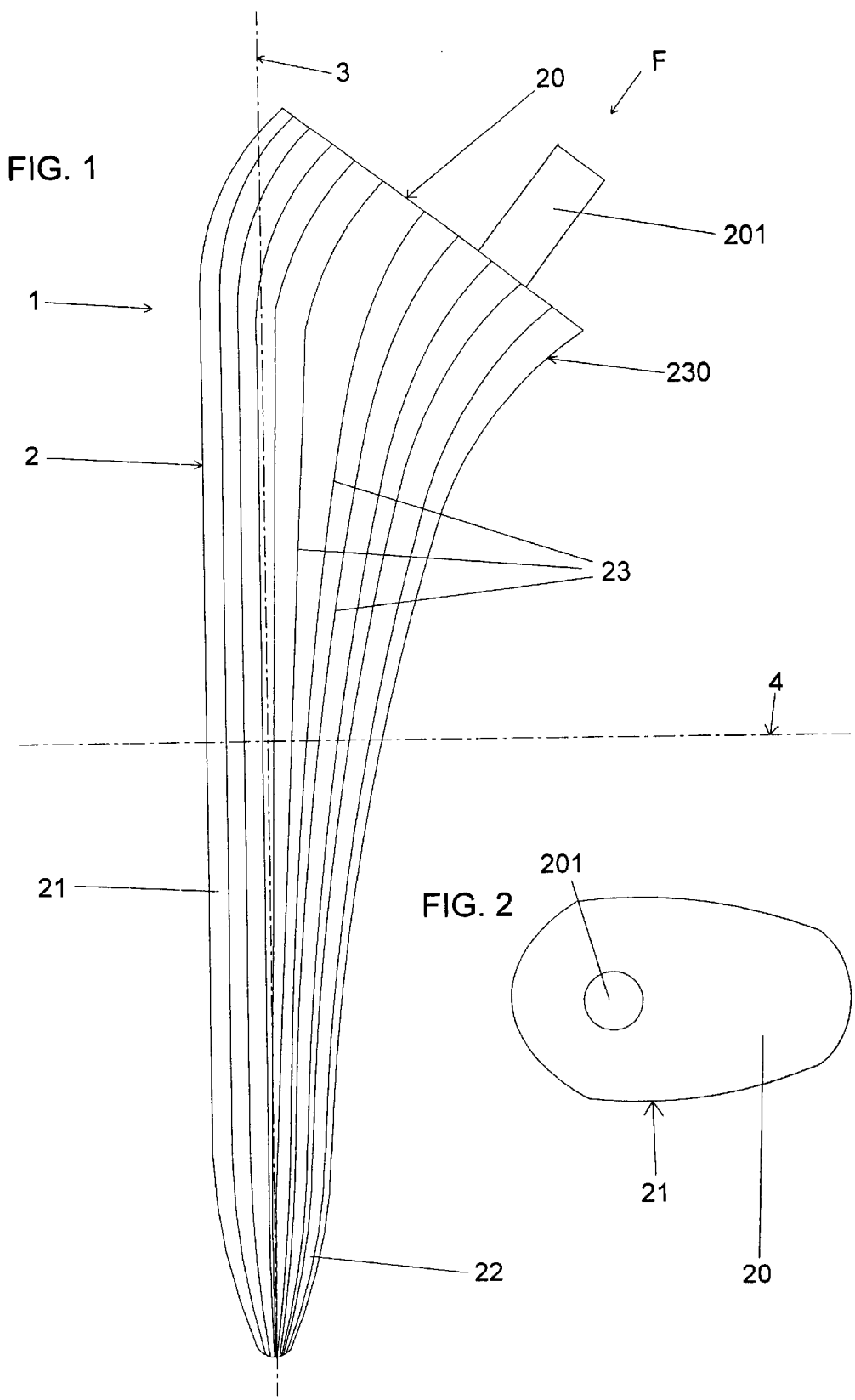

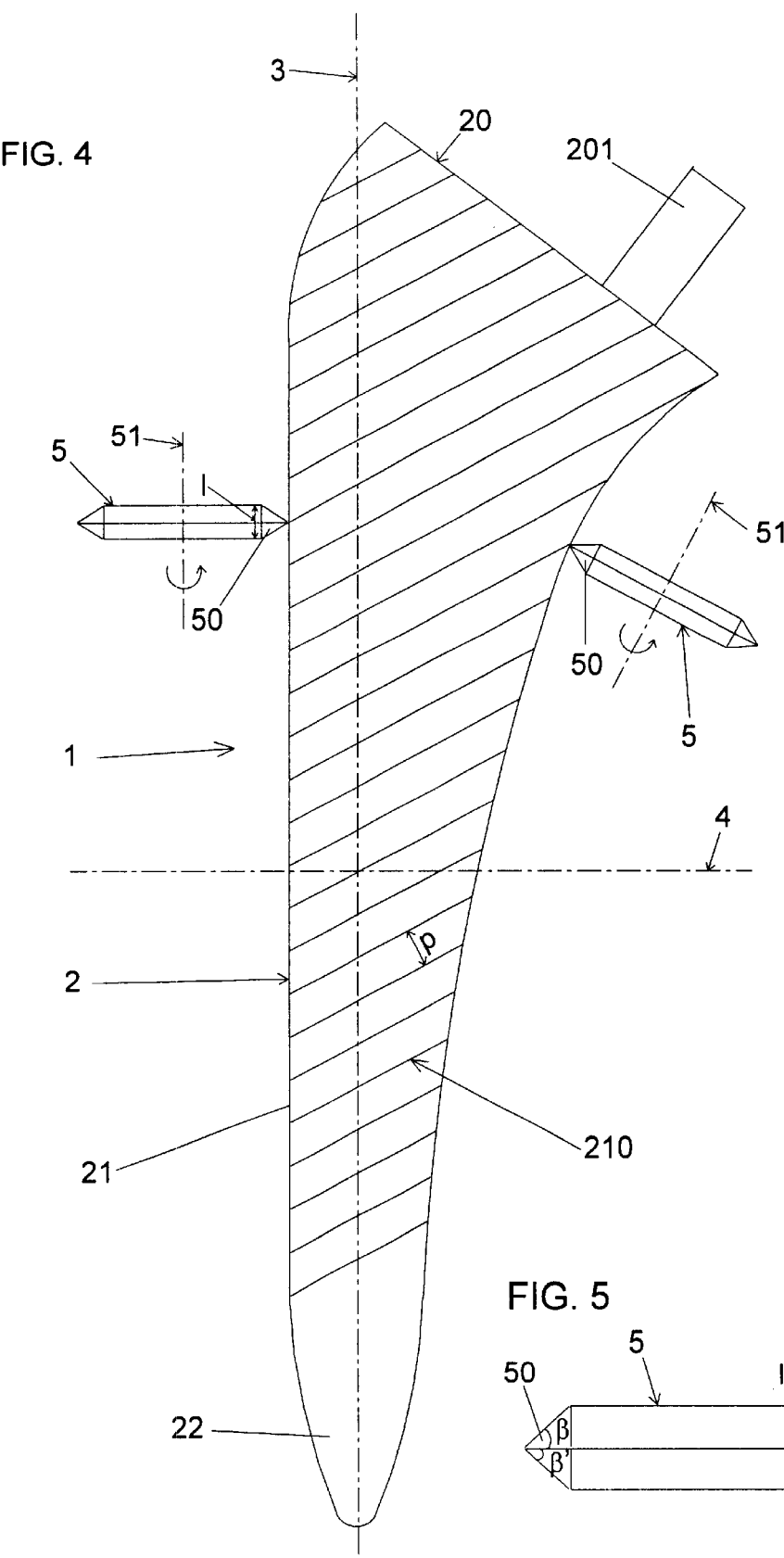
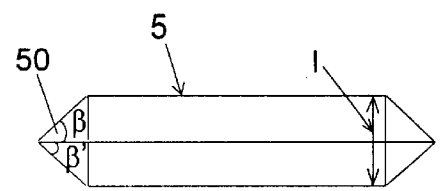

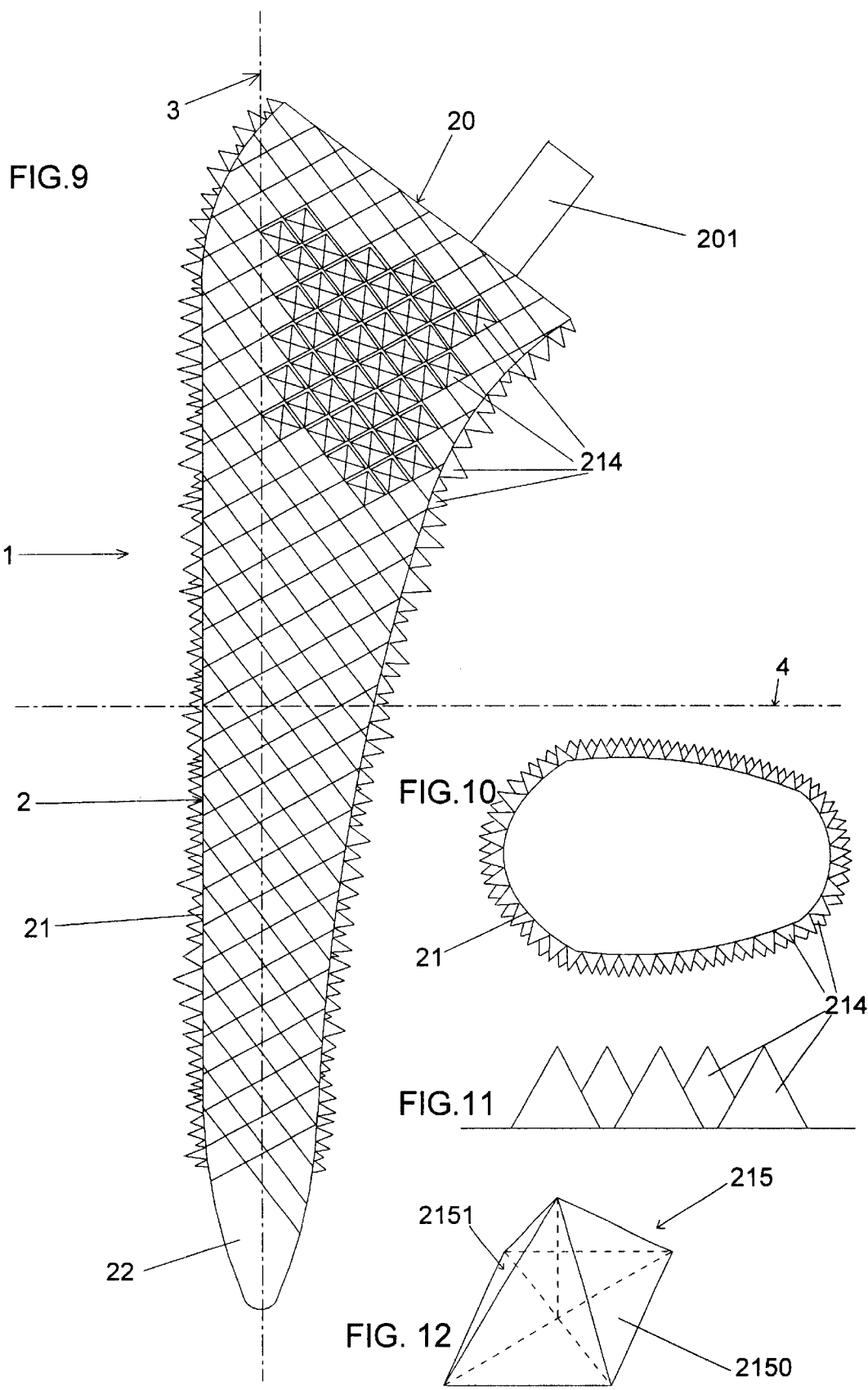

DEVICE FOR RASPING THE INTRAMEDULLARY CANAL OF A BONE AND METHOD FOR MANUFACTURING THE DEVICE

BACKGROUND OF THE INVENTION

The present invention relates to a device for rasping the intramedullary canal of a bone. The invention also concerns a method for manufacturing the device.

In articular arthroplasty, whatever the joint, there exist several types of prostheses which differ:

according to the pathology to be treated (trauma, arthrosis, malformation . . . ), according to the state of health of the patient, according to the type of approach first of all and the operating technique (anterior approach, posterior approach, with or without trochanterotomy . . . ), able to bring about modifications with respect to:

the type of geometry of the prosthesis (self-blocking form or not, anatomic or straight, with or without supporting plate, ovoid or rectangular cross-section . . . ), the type of fixation (with or without cement, with or without coating . . . ).

Surgeons need to adapt the preparation of the intramedullary canal of the bone depending on the type of prosthesis they will be using later, in order to operate efficiently and without risk, while still guaranteeing the reliability of the setting of the implant.

The medullary preparation or sizing of the bone is carried out using a broach. This shapes the intramedullary canal with precision so that the volume obtained corresponds with the volume of the implant to be set in place. In order to do this, the outer envelope of the broach is covered partially or totally by cutting teeth which will cut and consolidate the cancellous and cortical bone.

At present there are three families of cutting teeth more or less aggressive:

straight teeth, straight teeth with chip breaker, pyramid shaped diamond point teeth, These different types of cutting teeth are more or less well adapted to the medullar sizing required by the surgeon depending on the type of prosthesis chosen.

For these different types of cutting teeth, it is possible to vary the parameters of the teeth: cutting angle, flat tooth summit, pitch, orientation of the teeth.

Furthermore, for pyramidal teeth, it is possible to vary the angle of inclination of the faces of the pyramid. The point of the pyramid can thus be oriented in opposition to the cut.

According to brevet U.S. Pat. No. 5,665,091 a broach is known for preparing the intramedullary canal of a bone intended to receive a prosthesis. This broach comprises a longitudinal axis and is constituted of an anterior face, a posterior face and two lateral faces, one internal and one external face, communicating with the internal walls of the canal. Each face of the broach is provided with different cutting teeth for preparing the canal. Certain types of teeth, such as those called diamond point, are arranged in parallel rows inclined relative to the longitudinal axis of the broach. The different cutting teeth have different efficiencies, that is to say that they are more aggressive or less aggressive. If the teeth are not very aggressive, they will have a compacting effect in the bone. On the other hand, if they are very aggressive, they will have a cutting effect in the bone. The most aggressive are the diamond point teeth. On this type of broach, each type of teeth is arranged on one face of the broach depending on the bone quality of the zone of the internal wall of the intramedullary canal with which this face of the broach is in contact.

The problem with this type of broach rests in the fact that the spread of teeth over the surface is not homogeneous. In fact, methods making it possible to produce the different types of teeth are limited and often they do not allow certain types of teeth to be generated in certain zones of the broach or else the shape of the teeth, in these zones, is no longer under control, for example at the junction between two faces. Thus, the efficiency and precision of the sizing are not guaranteed and there is a high risk of the broach breaking, from the concentration of stresses when in service.

SUMMARY OF THE PRESENT INVENTION

The present invention therefore has the aim of compensating for these inconveniences of prior art by proposing a continuous machining method adapted to any shape whatever, making it possible to control the different types of teeth and the geometric properties of the teeth.

This aim is achieved by a machining method for obtaining cutting teeth on the surface of any shape whatsoever with a tool provided with a head, following at least one geometric curve traced on the envelope of said shape and having a helical form, characterised in that it comprises the following stages:

tracing the surface normal at a plurality of points taken along the helix, making the helix follow the head of the tool, orienting the head in such a way that it follows the orientation of the defined normals.

According to another particularity, the machining is carried out with a tool having a head of bevelled shape.

According to another particularity, the machining is carried out following a low inclination helix, in order to obtain a teeth with the appearance of the straight teeth type.

According to another particularity, the machining is carried out to different depths following several helices with different inclinations respectively, in order to obtain a chip-breaker teeth.

According to another particularity, the machining is carried out following two helices with inverse pitches, in order to obtain teeth with a base of the spaces formed by the intersections of the two helices.

According to another particularity, the machining is carried out following the two helices at the same depth, in order to obtain a diamond point type teeth, the orientation of the teeth being normal to the envelope.

According to another particularity, the pitches of the two helices are constant and equal, in order to obtain teeth with the shape of regular pyramids.

According to another particularity, the two helices have different inclinations so that the teeth formed by the passage of the tool are not aligned.

According to another particularity, the pitch of each helix is constant along the envelope of any shape whatsoever.

According to another particularity, the teeth can be flat or splayed on their upper part, by including inside the profile of the bevelled head of the tool a plane or splayed part.

Another aim of the invention is to propose a broach, whose manufacture requires the implementation of the method described above, on which the mechanical stresses when in service are spread over the whole surface of the broach and on which it is possible to obtain a homogeneous spread of teeth.

In order to achieve this aim, one uses the method described above for shaping a broach intended to prepare the intramedullary canal of a bone so that it can receive a prosthesis, the broach comprising a body, elongated along an axis closely parallel to the longitudinal axis of the canal, a variable transversal section, constituted of a face called the upper face and an external envelope, and having a shape capable of communicating with the internal wall of the intramedullary canal of the bone.

According to another particularity, the body of the broach ends in a profiled shape to aid pushing the broach into the canal.

According to another particularity, male or female elements, arranged on the upper face of the body constitute a system of locking mechanisms intended to receive an end piece constituting the extremity of a handle to manipulate the broach in the canal and intended eventually to receive trial prosthetic components.

According to another particularity, the upper face of the body is plane or comprises a pin making it possible to weld a handle for manipulating the broach in the bone.

DRAWING FIGURE DESCRIPTION

The invention, with its features and advantages, will become clearer by reading the description with reference to the attached drawings in which:

FIG. 1 shows, seen from the side, the broach according to the invention, on which several generatrix lines are traced, FIG. 2 shows, viewed from F, the upper face of the broach.

FIG. 3 shows a portion of the broach in perspective on which a portion of the helical curve is traced, FIG. 4 shows, seen from the side and simplified, the broach before machining, on which is traced a curve in the shape of a helix, FIG. 5 shows, from the side, the tool used for machining, FIG. 6 shows, in perspective, the body of a partially machined broach following a helix with constant pitch, FIG. 7 shows, seen from the side and simplified, the broach after machining, FIG. 8 shows, seen from the side and simplified, the broach on which two helical curves have been traced.

FIG. 9 shows, seen from the side and simplified, the broach after machining following two helical curves.

FIG. 10 shows a cross-section of the broach following the inclination of a helical curve after machining following two helical curves, FIG. 11 shows, seen from the side, the teeth obtained after machining following the two helices, FIG. 12 shows, in perspective, a tooth in the shape of a regular pyramid.

DESCRIPTION OF A PREFERRED EMBODIMENT

Figure 3:
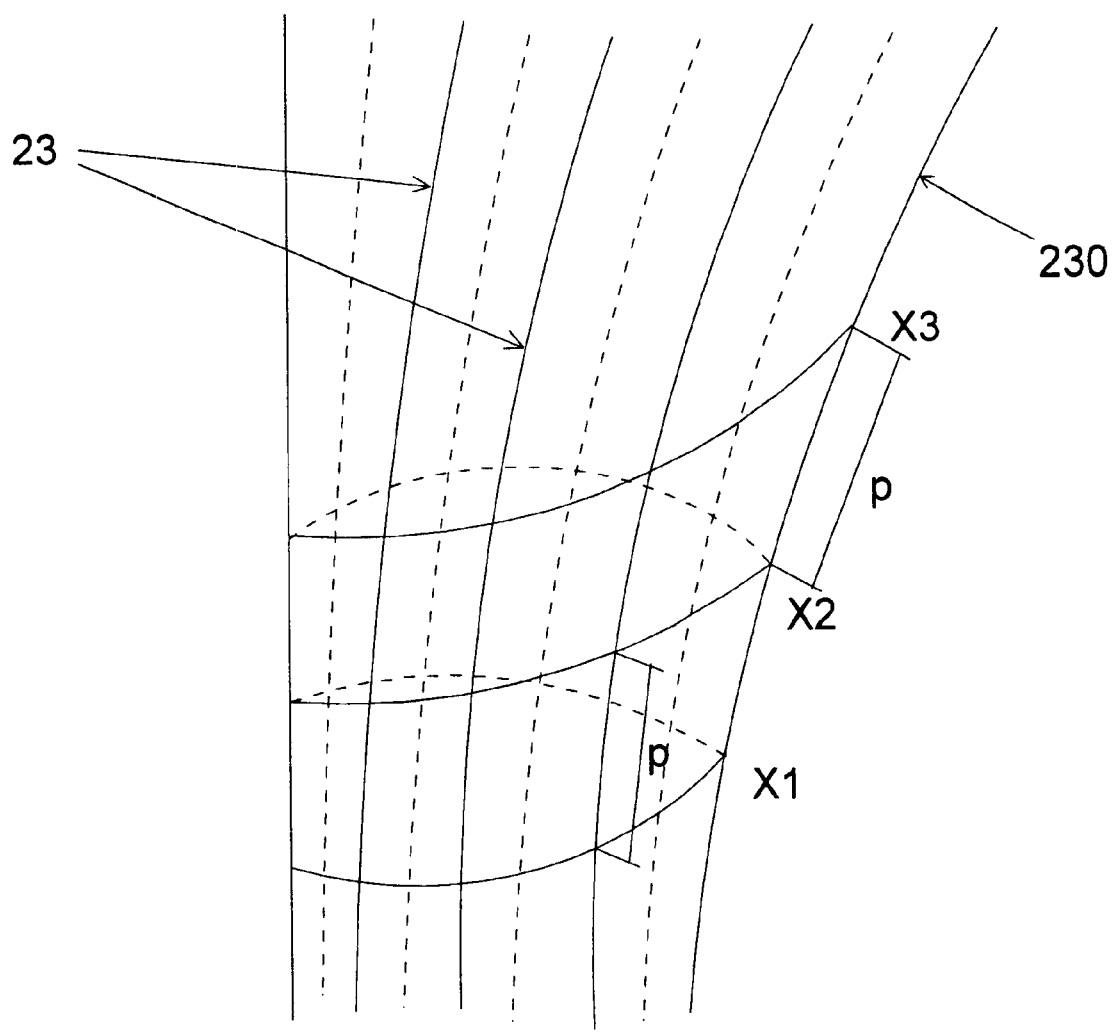

The broach according to the invention will first of all be described following FIGS. 1 to 7.

A broach 1, according to the invention, is intended to prepare the intramedullary canal of a bone in which a prosthesis is inserted. The broach 1 shown is suitable for sizing the canal of a femur. Each broach 1 has a variable shape depending on the shape of the intramedullary canal of the bone which the user wishes to prepare.

According to a known configuration, the broach is constituted of a body 2 comprising an upper face 20 and an external envelope 21 intended to rasp the internal wall of the canal. The body 2 ends by a profiled shape 22 intended to aid pushing the broach 1 into the canal. Geometric elements, such as pins 201, grooves or bores, male or female, arranged on the upper face 20 of the body 2 constitute a locking mechanism intended to receive an end piece constituting the extremity of a handle to manipulate the broach in the canal and intended eventually to receive the trial prosthetic components. The upper face 20 of the body 2 can be plane or can comprise a pin allowing welding of a handle for manipulating the broach 1 in the bone.

The body 2 of the broach 1 has an elongated shape along an axis 3 closely parallel to the longitudinal axis of the canal. The cross-section of the body 2 of the broach 1 is variable along the body 2, then reduces on its final extremity, to end by the profiled shape 22 intended to aid pushing the broach 1. The shape of the cross-section of the lower part of the broach 1 is closely constant. On the upper part of the body 2 of the broach 1, the shape of the cross-section of the body 2 is progressively variable and greater than the cross-section of the lower part of the body 2. The junction between the lower part and the upper part is produced by a continuity of the curves forming the surfaces. The upper face 20 of the body 2 is inclined relative to the axis 3 of the broach 1.

According to a first variant, a machining following a geometrical curve with a helical shape 210 is carried out on the external wall 21 of the body 2 of the broach 1.

Figure 6:
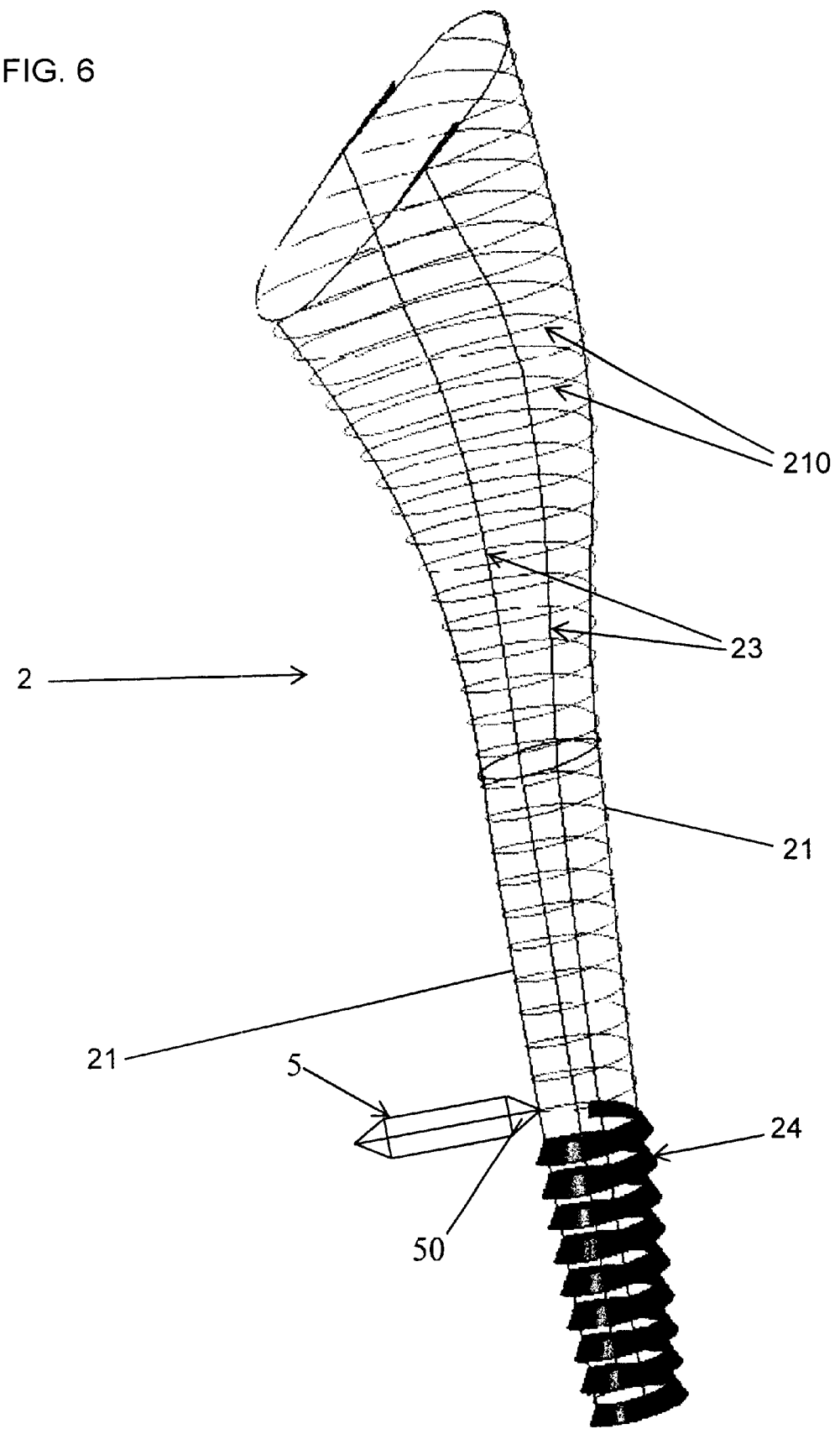

In order to do this, the helical curve 210 is first of all drawn on the external envelope 21 of the body 2 of the broach 1 with the aid of a software programme. This software makes it possible to construct helices with constant or variable pitch of any shape whatsoever coming from a broach. The software uses the following method for constructing a helix on any shape whatsoever, such as that of the broach 1 of the invention. The shape of the body 2 of the broach is defined by generatrix lines 23 according to the envelope surface 21 as shown in FIGS. 1 and 3. On a generatrix line 230 of the body 2 of the broach 1, several points are positioned, distant from each other by a constant pitch, defined by p of the helical curve one wishes to trace. In FIG. 3, starting from one of these points, defined by X1, a portion of the helix is traced around a complete revolution of the shape of the broach, the portion of the helix joining the point of the generatrix line adjacent to X1, for example upper, being defined by X2. Continuing the first helical portion a second helical portion is traced, joining X2 at the point of the generatrix line higher than X2, defined by X3. This operation is reproduced with a third helical portion and continues in this way, so that the whole envelope 21 is covered by a continuous helical curve 210 with constant pitch. Thus we obtain a broach with a helical curve 210 traced on it, as shown in FIG. 6. In a variant, one can imagine a helix with variable pitch along the body 2 of the broach 1.

FIG. 4 is a simplified drawing of the broach on which a helical curve with constant pitch is traced. In fact, the pitch of the helical curve to be shown being constant and the cross-section of the body 2 of the broach 1 being variable, the angle of the helical curve, defined relative to the axis 4 perpendicular to the axis 3 of the broach 1 is not, in reality, constant as shown in this figure. The cross-section in the upper part of the body 2 of the broach 1 being greater than that of the lower part of the body 2 of the broach 1, the helical curve angle varies decreasingly from the bottom to the top of the body 2 of the broach 1. The illustrations are also simplified in FIGS. 7, 8 and 9.

In the case of a constant pitch, the helical curve angle is variable along the body 2 of the broach 1, but nonetheless one refers to helical inclination corresponding to the maximum angle of the helical curve. This angle is at its maximum where the cross-section of the body 2 of the broach 1 is smallest, that is to say on the lower part of the body 2 of the broach 1.

When the helix 210 has been drawn, machining can begin following the trace of the helical curve, as shown in FIG. 6. The machining is carried out with a tool 5, shown in FIG. 5, burr or grinder, with a bevelled front head 50. This head 50 can have different widths l and a bevel whose angle, defined by β and β' equal or different, can vary according to the efficiency required for the broach 1. The machining depth varies in function of the width l and the angle of the bevelled head. The burr or grinder is rotated around an axis 51 permanently maintained parallel to the tangents at the points belonging to the successive generatrix lines 23 and forming a helical curve 210, as shown in FIGS. 4 and 6.

In a first stage, at each point of the helix 210, the software traces the surface normals of the external envelope 21 of the body 2. Next, the tool 5 machines the external envelope 21 of the body 2 of the broach 1 following the traced helix 210, the head 50 of the tool 5 being oriented in such a way as to follow the orientation of the traced normals. This machining is carried out on a machine comprising at least five axes.

Figure 7:
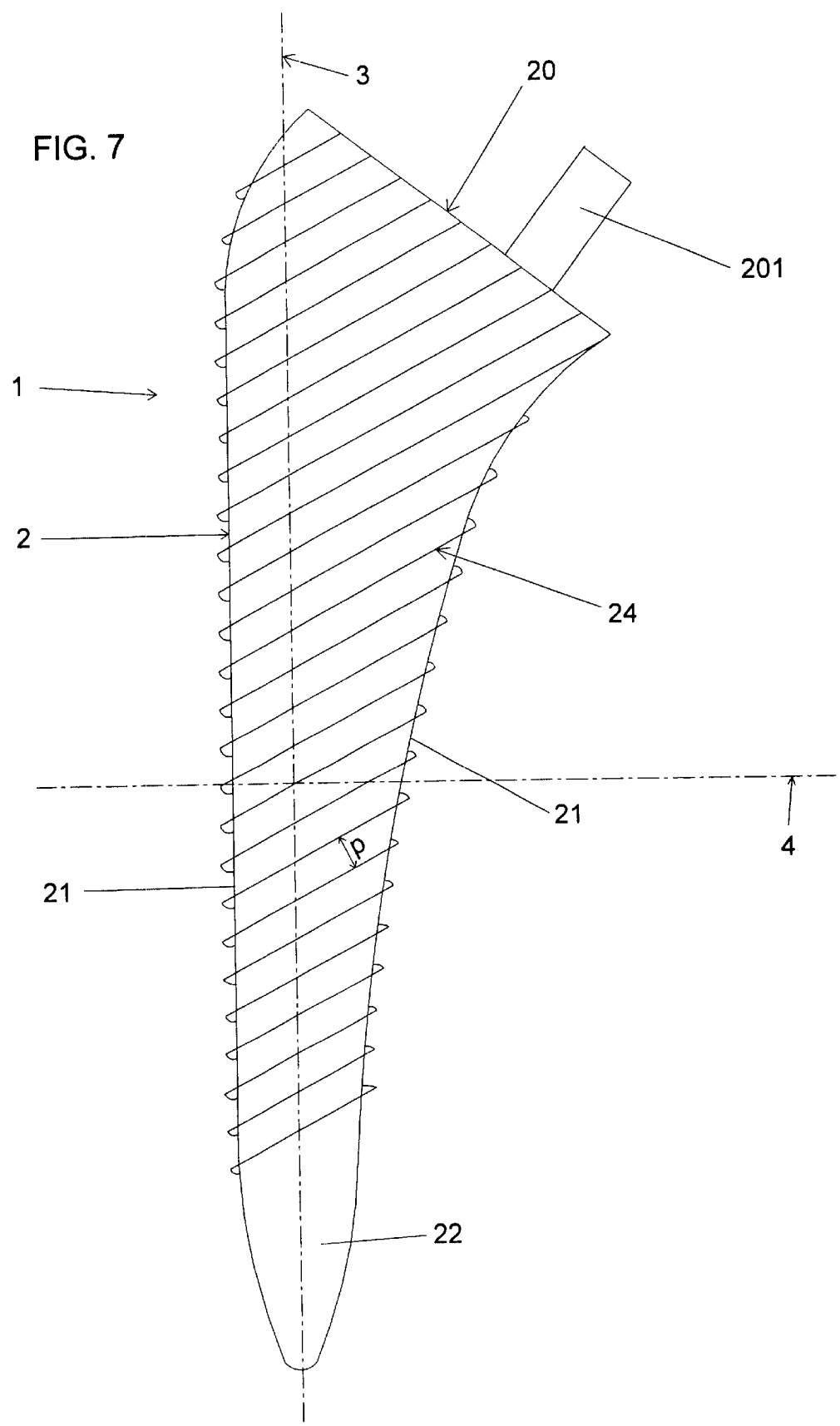

Once the machining following the helix 210 is finished, the body 2 of the broach 1 has a thread 24 as shown in FIGS. 6 and 7. This thread profile 24 makes it possible to limit rupture risks, since the work stresses are no longer concentrated only on the weakest cross-section but are spread over the whole of the height of the teeth. Furthermore, the continuous helical machining makes it possible to avoid sizing suppressions with respect to the close physiological environment thus limiting the risk of fat embolism when the broach is used, since the clearance outlet of bone chips is still open.

In the case where the machining is carried out following a helix 210 of low inclination, the broach then has a teeth of the straight teeth type.

The width of the head 50 of the tool 5 in bevelled shape, defined by l, can for example be closely equal to or greater than the pitch p of the helix 210, in order to form a thread 24 which is cutting and therefore more efficient.

The pitch of the helix 210 can, for example, be variable along the body 2 of the broach 1.

It is possible to machine the broach according to several helices of different inclinations and spread along the axis 3 of the broach 1. In this case, the machining can be carried out at a different depth for each helix to form a so-called chip-breaker teeth.

According to a second variant, the machining is carried out following two helical curves 211, 212 on the external envelope 21 of the body 2 of the broach 1.

The invention will now be described with reference to FIGS. 8 to 12.

Two helical curves 211, 212 are first of all traced according to the method described above, as shown in FIG. 8. These helices 211, 212 have the special property of being inverse. Preferably they have different inclinations relative to the axis 4. The two helices 211, 212 can have constant pitches, p' and p" respectively, equal or different. The spaces 213 thus formed by the intersection of the two helices 211, 212 are even and spread homogeneously over the whole surface of the body 2 of the broach 1.

Figure 8:
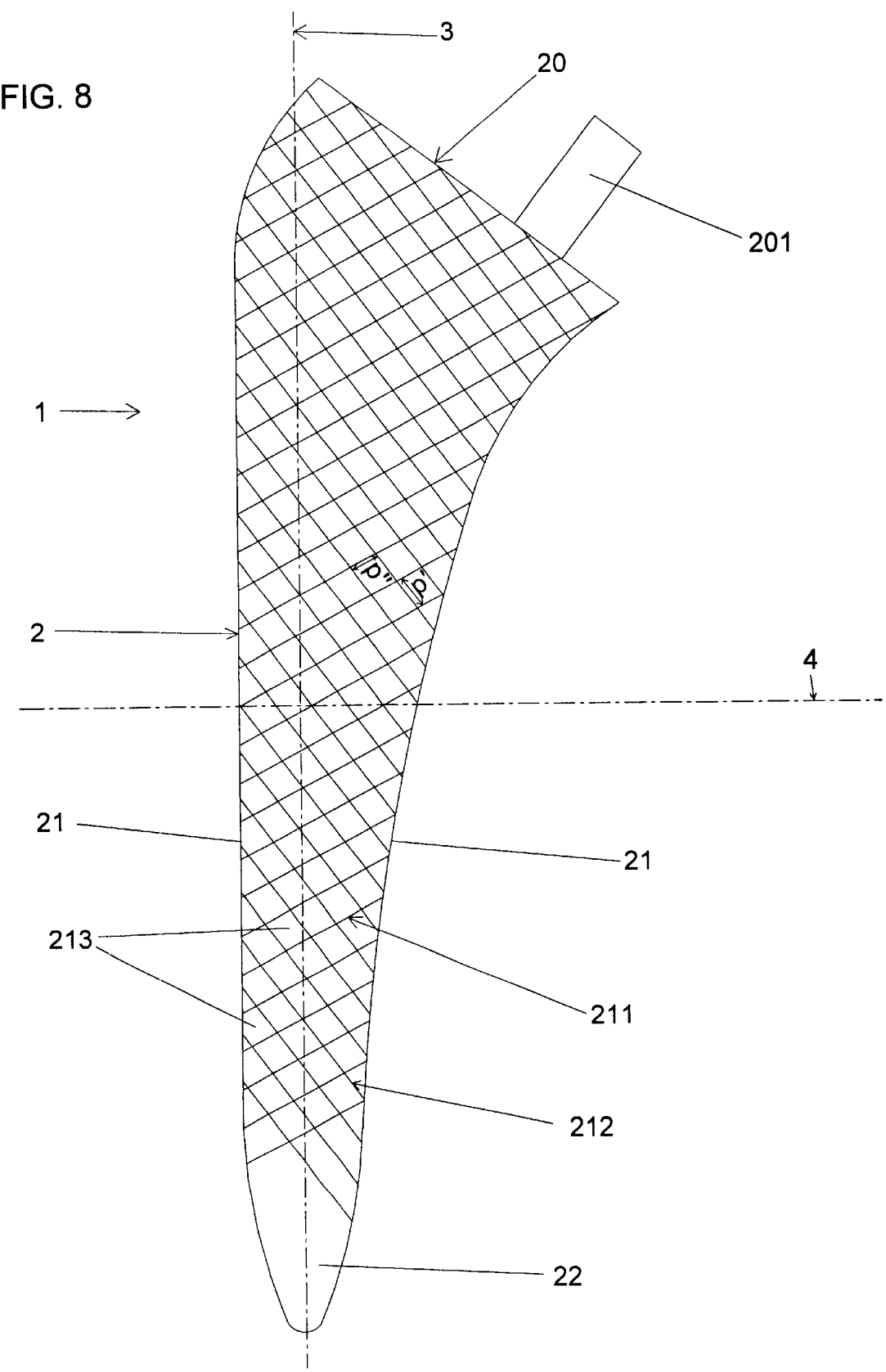

The two machining operations are carried out according to the method described above. The head 50 of the tool 5 is chosen so that its width l is closely equal to or greater than the pitch p', p" of the helix 211, 212 which it follows in order to form, after machining, a cutting thread. Machining with this tool 5 following the two helices 211, 212 with inverse pitches will thus form teeth 214, as shown in FIG. 8. These teeth 214, because of the bevelled shape of the head 50 of the tool 5, with β and β' equal and in the case of a penetration depth of the tool 5 and equal following the two helices 211, 212, of equal pitches p' and p", are points in the shape of regular pyramids 215, as shown in FIGS. 11 and 12. These pyramids 215 have for base 2150 the spaces 213 formed by the intersections of the two helices 211, 212 of inverse pitches and their height is normal to the surface of the body 2 of the broach 1. These teeth 214 in regular pyramid shape 215 are diamond points and are very aggressive. The angle of the bevelled head 50 defined by β and β' can, for example, be 90° in order to form pyramids 215 whose lateral faces 2151 make an angle of 45° with the base.

It is possible to produce pyramids which are flat or splayed on their upper part by including a flat or splayed part in the profile of the bevelled head 50 of the tool 5.

In the case where the inclinations of the inverse helices are chosen to be different, this makes it possible to avoid the pyramidal teeth 214 being aligned along the axis 3 of the broach 1. By displacing the position of the teeth 214 placed one on top of the other, a complete sizing of all the intramedullary wall corresponding with the implant is carried out, avoiding the formation of vertical stria in the bone.

One can choose to incline the head 50 of the tool 5 relative to its position normal to the surface, in order to form uneven pyramids in certain parts of the broach. Also, the angle of the bevelled head 50 can vary from one machining to another by playing on the size of the angles β and β' of the bevel head, that is to say with β different from β' it is possible to obtain uneven pyramids with displaced summits.

According to another variant, the pitches p' and p" of each helix 211, 212 are not constant and vary along the body 2 of the broach 1. In this latter case, the section 213 constituting the base of the teeth 214 will be variable depending on the evolution of pitches p' and p".

According to another variant, the two machining depths following the two helices 211, 212 respectively, are different, in such a way as to create a chip-breaker teeth.

This machining following two helices with inverse pitches thus makes it possible to obtain a homogeneous spread of teeth 214 over the whole external envelope 21 of the body 2 of the broach 1 and in particular at the more rounded junction points of the envelope 21. Thus, the sizing of the internal wall of the intramedullary canal will be complete and homogeneous, the whole surface corresponding to the implant will have been worked.

In FIG. 9, the height of the teeth is shown as uneven since the highest teeth 214 are those in the front and the lowest those in the back. It is to be understood that, compared with the contour of a broach 1 corresponding to a section following the inclination of a helix 211, 212 as shown in FIG. 9, the height of the teeth 214 is constant on this contour in the case where the two pitches p' and p" are constant and the penetration of the tool 5 as well.

A broach according to the invention machined following two helices will, for example, have the following properties. The broach can be in heat-treated stainless steel X5 Cr Ni Cu Nb 16.04. It can be of length L of 150 mm, a cross-section D of 12 mm, a pitch p' of 3 mm, a pitch p" of 3 mm as well, angles α' and α" of 30° and 50° respectively and a radius of tooth base of 0.5 mm.

It must be evident to those skilled in the art that the present invention permits modes of implementation under many other specific forms without departing from the field of application of the claimed invention. Consequently, the present modes of implementation must be considered as illustrative examples, but can be modified in the domain defined by the range of the attached claims, and the invention must in no way be limited to the details given above.

What is claimed is:

1. A machining method for obtaining cutting teeth on an external surface of a non-flat object by a tool having a head for removing material from the object and following at least one geometric curve having the form of a helix traced on the external surface of the object, comprising the steps of:

tracing a surface normal at a plurality of points that belong to the helix along the external surface of the object; and moving the head of the tool along the helix while orienting the head to remain in the same orientation with respect to each surface normal at each said plurality of points forming a helix to machine the object and thereby form the cutting teeth.

2. A machining method according to claim 1 wherein the head of the tool has a bevel.

3. A machining method according to claim 2 including forming a helix having a low inclination about an axis of the object to obtain teeth with the appearance of a straight shape.

4. A machining method according to claim 2 including providing a plurality of geometric curves in the form of helices traced on the external surface of the object at different inclinations and machining the object at different depths, respectively, following the plurality of helices of different inclinations to obtain chip breaker teeth.

5. A machining method according to claim 2 including providing two geometric curves in the form of two helices having inverse pitches traced on the external surface of the object and machining the object by following the two helices of inverse pitches to obtain teeth having bases formed by the intersections of the two helices.

6. A machining method according to claim 5 including machining the object by following the two helices at the same depth in the object to obtain teeth having a diamond point shape and oriented normal to the external surface of the object.

7. A machining method according to claim 6 including providing the two helices with constant and equal pitches to obtain teeth having the general shape of regular pyramids.

8. A machining method according to claim 2 wherein the object is a broach including providing two geometric curves in the form of two helices, respectively, at different inclinations about the object such that the formed teeth are not aligned along an axis of the broach.

9. A machining method according to claim 6 including forming the pitch of each helix constant along the length of the external surface of the object.

10. A machining method according to claim 5 including providing a flat or round part in the profile of the beveled head of the tool.

11. A method according to claim 1 including forming a broach for the preparation of an intramedullary canal of a bone for reception of a prosthesis wherein the broach includes a body elongated along an axis generally parallel to a longitudinal axis of the canal, and with a variable cross-section, the body having an upper face and an external shape generally corresponding to the shape of an internal wall of an intramedullary canal of the bone.

12. A method according to claim 11 including forming a profiled shape along an end of the body of the broach to facilitate pushing of the broach into the canal.

13. A method according to claim 11 including forming a locking mechanism along the upper face of the body for receiving an endpiece constituting a handle for manipulating the broach in the canal.

14. A method according to claim 11 including forming a pin on an otherwise flat upper face of the body enabling attachment of a handle to the broach to manipulate the broach in the bone.

* * * * *